United States Patent [19]

Kato et al.

[11] Patent Number: 4,492,757
[45] Date of Patent: Jan. 8, 1985

[54] PROCESS FOR PREPARING L-THREONINE

[75] Inventors: Masaaki Kato; Teruzo Miyoshi; Iwao Kibayashi, all of Machida; Masahisa Ikemi, Tokyo; Haruo Gomi, Machida; Yoshiaki Ishimatsu, Zama; Noriaki Koizumi, Ibaraki; Hideaki Yamada, Kyoto, all of Japan

[73] Assignee: Denki Kagaku Kogyo Kabushiki Kaisha, Tokyo, Japan

[21] Appl. No.: 449,216

[22] Filed: Dec. 13, 1982

[30] Foreign Application Priority Data

Dec. 28, 1981 [JP] Japan .................................. 56-209984
Dec. 28, 1981 [JP] Japan .................................. 56-209985

[51] Int. Cl.$^3$ .......................... C07B 19/02; C12P 13/08
[52] U.S. Cl. ....................................... 435/280; 435/115
[58] Field of Search ................................ 435/115, 280

[56] References Cited

FOREIGN PATENT DOCUMENTS 56-121491 9/1981 Japan .................................. 435/115

OTHER PUBLICATIONS

"Bacterial Catabolism of Threonine. Threonine Degradation Initiated by L-Threonine Acetaldehyde-Lyase (Aldolase) in Species of Pseudomonas" Bell, Stephen C. and Turner, John M., *Chemical Abstracts* 87, p. 282 (180420q) (1977).

"Bacterial Catabolism of Threonine. Threonine Degradation Initiated by L-Threonine Acetaldehyde-Lyase (Aldolase) in Species of Pseudomonas" Bell, Stephen C. and Turner, John M., *Biochem. J.* 166, pp. 209-216 (1977).

"L-Serine Dehydratase, DL-Threonine Aldolase, and D-Glucuronate Reductase in Serum. Effects Following Experimental Liver and Kidney Damage in the Rat" Lee, L. P. K., and Bernstein, I. A., *Chemical Abstracts* 69, p. 875 (9318s) (1968).

*Primary Examiner*—Lionel M. Shapiro
*Attorney, Agent, or Firm*—Oblon, Fisher, Spivak, McClelland & Maier

[57] ABSTRACT

Disclosed is a process for preparing L-threonine which comprises causing D-threonine-aldolase, or D-threonine-aldolase and L-allothreonine-aldolase to act on a solution containing at least DL-threonine thereby obtaining L-threonine from a mixture containing at least DL-threonine.

9 Claims, No Drawings

PROCESS FOR PREPARING L-THREONINE

BACKGROUND AND DETAILED DESCRIPTION OF THE INVENTION

The present invention relates to a process for preparing L-threonine which comprises causing D-threonine-aldolase, or D-threonine-aldolase and L-allothreonine-aldolase to act on a solution containing at least DL-threonine.

More particularly, the present invention relates to a process for preparing L-threonine which comprises causing D-threonine-aldolase to act on DL-threonine or causing D-threoninealdolase and L-allothreonine-aldolase to act on a mixture of DL-threonine and DL-allothreonine thereby obtaining L-threonine from DL-threonine or the mixture of DL-threonine and DL-allothreonine by decomposing D-threonine, D-allothreonine and L-allothreonine asymmetrically into glycine and acetaldehyde.

L-threonine is one of the essential amino acids for human and animals, and because of the relatively small content thereof in various animal and plant proteins, the potential demand for L-threonine as one of the additives into foods and feeds is large enough. Hitherto, L-threonine has been produced by a method of extraction from natural materials or a method of fermentation of natural materials, however, due to the relatively high cost of L-threonine produced by such a method, a process for preparing thereof at a lower cost has been required.

On the other hand, although L-threonine is easily synthesizable while using glycine, etc., D-threonine is by-produced in the same amount as that of L-threonine with the simultaneous formation of D-allothreonine and L-allothreonine as their DL-isomer. Accordingly, the steps of isolating and pruifying L-threonine from the reaction products are extremely complicated. The yield of L-threonine is low and the price of L-threonine produced by synthetic process is very high. For instance, as an optical resolution method of DL-threonine, the methods disclosed in Bull.Soc.Chim., Vol. 20, page 903(1953) and ibid., Vol. 23, page 447(1956) have been known, however, these methods for optical resolution of DL-threonine are extremely troublesome and only give L-threonine in a low yield. In addition, for removing allothreonines, a very troublesome and inefficient method is inevitably used such as the method disclosed in Japanese Patent Publication No. 36-19562(1961) wherein bis(acetaldehyde)threonine copper is used, or the method disclosed in U.S. Pat. No. 2,461,847 wherein allothreonine and threonine are converted into their sodium salts in ethanol by using sodium ethylate, and the salts are separated by utilizing the difference between their solubilities.

Besides, there have been demerits in the synthetic process that there are scarcely any demand for D-threonine and allothreonine in the market, and that the racemization of D-threonine into L-threonine is not so easily effected.

As a result of the present inventors' efforts in studying for developing a process for preparing L-threonine at a low cost by utilizing enzymatic reactions while dissolving the technical problems, the present inventors have found a novel enzyme which catalyzes D-threonine and also D-allothreonine to convert them into glycine and acetaldehyde, and termed the enzyme D-threonine-aldolase. Namely, the present inventors have further found that in the case where D-threonine-aldolase is brought into action on the product of the synthesis, i.e., DL-threonine, or in the case where D-threonine-aldolase in combination with L-allothreonine-aldolase is brought into action on the more complicated products of synthesis, i.e., a mixture of DL-threonine and DL-allothreonine, L-threonine together with the useful decomposition-product, i.e., glycine and acetaldehyde are obtained. As the result, the preparation of L-threonine is easily carried out and the by-products are utilizable while dissolving all the problems shown above.

In an aspect of the present invention, there is provided a process for preparing L-threonine which comprises causing D-threonine-aldolase or D-threonine-aldolase and L-allothreonine-aldolase to act on a solution containing at least DL-threonine. More particularly, there is provided a process for preparing L-threonine which comprises causing D-threonine-aldolase to act on DL-threonine or causing D-threonine-aldolase and L-allothreonine-aldolase to act on a mixture of DL-threonine and DL-allothreonine thereby obtaining L-threonine from DL-threonine or the mixture of DL-threonine and DL-allothreonine.

Namely, the present invention relates to a process for obtaining L-threonine from DL-threonine or a mixture of DL-threonine and DL-allothreonine, comprising the step of catalyzing DL-threonine contained in an aqueous solution with D-threonine-aldolase or catalyzing a mixture of DL-threonine and DL-allothreonine contained in an aqueous solution with a mixture of the D-threonine-aldolase and L-allothreonine-aldolase.

The D-threonine-aldolase according to the present invention is a novel enzyme which decomposes D-threonine into glycine and acetaldehyde and also catalyzes D-allothreonine to decompose thereof into glycine and acetaldehyde. An enzyme produced by a strain of *Alcaligenes faecalis*, IFO 12669 (deposited in Institute for Fermentation Osaka, Japan), an enzyme produced by a strain of Pseudomonas DK-2, deposited in Fermentation Research Institute, Agency of Industrial Science and Technology, Ministry of International Trade and Industry, Japan under a deposite number of FERM-P No. 6200, and an enzyme produced by a strain of Arthrobacter DK-19, also deposited in the latter Institute under a deposite number of FERM-P No. 6201 respectively possess an activity of deocmposing D-threonine and D-allothreonine and accordingly, each of them can be used according to the present invention.

The bacteriological properties of the strain of Pseudomonas DK-2 (FERM-P No. 6200) and the strain of Arthrobacter DK-19 (FERM-P No. 6201) are shown below.

| (a) Morphological properties: | | |
| --- | --- | --- |
| Item | Pseudomonas DK-2 | Arthrobacter DK-19 |
| Shape of cells | rod-shaped | rod-shaped |
| Size of cells ($\mu$) | 1.5 × 0.8 | 2.5 × 0.8 |
| Pleiomorphism | none | Mixture of rods of ordinary curved line-like ones, V-shaped ones and stick-like ones |
| Mobility | positive monotrichous | positive: very active peritrichous |
| Spore | none | none |
| Gram-staining | negative | having gram-positive granules within the gram-negative cells |

-continued (a) Morphological properties:

| Item | Pseudomonas DK-2 | Arthrobacter DK-19 |
|---|---|---|
| Acid-fastness | none | none |

(b) Growth state in various culture media:

| Item | Pseudomonas DK-2 | Arthrobacter DK-19 |
|---|---|---|
| Plate culture medium of agar with bouillon | semi-transparent circular colonies with convex-circular protuberance, lustrous | semi-transparent cream-coloured circular colonies with convex-circular protuberance, lustrous |
| Slunt culture of agar with bouillon | growth moderate, semi-transparent and lustrous | growth moderate, semi-transparent thread-like colonies with cream-like colour, lustrous |
| Liquid culture medium with bouillon | growth moderate | growth favorable flocculent |
| Stab culture with gelatin and bouillon | growth favorable on the surface of the culture medium | growth favorable on the surface of the culture medium as filiform |
| Litmus-milk | change to alkaline color | discoloration without liquefying |

(c) Physiological properties:

| Item | Pseudomonas DK-2 | | Arthrobacter DK-19 | |
|---|---|---|---|---|
| Reduction of nitrate | + | | − | |
| Denitrification | + | | + | |
| MR test | − | | − | |
| VP test | − | | − | |
| Production of indole | − | | − | |
| Production of H$_2$S | +(weak) | | +(weak) | |
| Hydrolysis of starch | − | | − | |
| Utilization of citric acid in | | | | |
| Koser's medium | − | | + | |
| Christensen's medium | − | | + | |
| Utilization of inorg. nitrogen source | | | | |
| nitrate | − | | − | |
| ammonium salt | − | | − | |
| Production of dye | − | | − | |
| Activity as urease | − | | − | |
| Activity as oxidase | + | | − | |
| Activity as catalase | + | | + | |
| Range of growth | | | | |
| pH | 6 to 9.5 | | 4.5 to 9.5, preferably 8 to 8.5 | |
| temperature (°C.) | 5 to 50 | | 15 to 38, preferably 28 to 30 | |
| Aerobism | yes | | yes | |
| O-F test (method of Hush Leifson) | oxidative | | oxidative | |
| Production of acid and gas from sugar | acid | gas | acid | gas |
| L-arabinose | − | − | − | − |
| D-xylose | − | − | − | − |
| D-glucose | − | − | − | − |
| D-mannose | − | − | − | − |
| D-fructose | − | − | − | − |
| D-galactose | − | − | − | − |
| Maltose | − | − | − | − |
| Sacrose | − | − | − | − |
| Lactose | − | − | − | − |
| Trehalose | − | − | − | − |
| D-solbitol | − | − | − | − |
| D-mannitol | − | − | − | − |
| Inositol | − | − | − | − |
| Glycerol | +(weak) | − | − | − |
| Starch | − | − | − | − |
| Raffinose | − | − | − | − |
| Inulin | − | − | − | − |
| D-ribose | − | − | − | − |
| Dulcitol | − | − | − | − |
| Sorbose | − | − | − | − |
| Carboxymethyl-cellulose | − | − | − | − |
| Halotolerance in | | | | |
| 5% by weight of aqeuous solution of sodium chloride | does grow | | does grow | |
| 10% by weight of aqueous solution of sodium chloride | does not grow | | does grow slightly | |
| Decompositive activity to gelatine | − | | − | |
| Activity as DNA-ase | − | | − | |
| Essential vitamins | thiamine and folic acid | | pantothenic acid and nicotinic acid | |
| Source of isolation | soil | | soil | |

On classifying these two strains on the ground of the bacteriological properties while referring to "Manual of Determinative Bacteriology, 8th Ed. (1974)" by Burgey, the strain DK-2 was identified to belong to the genus Pseudomonas, because it is a gram-negative rod which is monotrichous, positive in oxidase activity and positive in denitrification.

On the other hand, the strain DK-19 was identified to belong to the genus Arthrobacter, because it is a weakly grampositive rod having a pleiomorphism and is peritrichous and impossible to utilize saccharide.

The enzyme having both the activity of D-threonine-aldolase and the activity of D-allothreonine-aldolase according to the present invention can be produced by culturing, for instance, one of the strains in a nutrient culture medium which may be the same as those for culturing ordinarily any strain of bacterial containing saccharide such as glucose, glycerol, molasses and the like or organic carboxylic acid such as acetic acid, malic acid and the like as a carbon source, ammonium sulfate, ammonium chloride, urea and the like as a nitrogen source, yeast extract, pepton, meat extract, corn-steep liquor, etc. As an organic nutrient and magnesium, iron, manganese, potassium, phosphate, etc. as inorganic ion. The cultivation may be effected under the conventional conditions, that is, at a pH of 4 to 10 of the culture medium, at a temperature of 20° to 60° C. for 1 to 3 days of aerobic cultivation after being inoculated.

By culturing one of the strain under the conditions, the enzyme having both the activity of D-threonine-aldolase and the activity of D-allothreonine-aldolase is produced in the bacterial bodies and accumulated therewithin. In order to isolate the enzyme in a purer state from the cultured medium thereof, the proliferated bodies of the strain of microorganism (hereinafter referred to as "the bacterial cells") are destroyed by a known method such as a mechanical method, a treatment with an enzyme and an autolysing method to obtain a crude extract of the enzyme and then the crude extract was subjected to purification by a suitable combination of precipitation with ammonium sulfate or an organic solvent such as acetone or methanol, and chromatography while using an ion-exchanger such as diethylaminoethyl (hereinafter referred to as "DEAE")cephalose, DEAE-cephadex and calcium phosphate gel, etc. or an adsorbent, etc. In order to obtain the manifastation the enzymic activity thereof, the presence of a coenzyme, pyridoxal-5'-phosphate, is necessary in its reaction in an ordinary amount of $10^{-5}$ to $10^{-3}$M.

Physico-chemical properties of the novel enzyme according to the present invention are explained as follows.

(1) Activity and substrate-specificity:

The novel enzyme according to the present invention decomposes both D-threonine and D-allothreonine into glycine and acetaldehyde, and on the other hand, does not act at all on L-threonine and L-allothreonine.

(2) Optimum pH:

From the result of determination of aldehyde produced by the novel enzyme from D-threonine as a substrate at 30° C. for 10 min. at one of a series of pH, it is found that the optimum pH of the novel enzyme was in a range of 7 to 9. The respective buffer solutions used are a 0.1M phosphate buffer for a range of pH of 4 to 7.5, a 0.1M tris-HCl buffer for a range of pH of 7 to 9 and a 0.1M sodium carbonate buffer for a range of 9 to 11.

(3) pH range in which the novel enzyme is stable:

From the result of determination of the remaining activity of the novel enzyme after heating a solution of the enzyme for one hour at 30° C. at one of a series of pH, the pH range in which the novel enzyme can exist in a stable state is 6 to 9. The respective buffer solution used in the calturing are a 1.0M phosphate buffer for a range of pH of 4 to 7.5, a 0.1M tris-HCl buffer for a range of pH of 7 to 9 and a 0.1M sodium carbonate buffer for a range of 9 to 11.

(4) Method for determination of the enzymic activity:

The amount of acetaldehyde formed when 0.1 ml of a liquid containing the novel enzyme is added to 0.4 ml of a 0.1M tris-HCl buffer solution containing 100 micromols of D-threonine at pH of 8.0 and the mixture is heated at 30° C. for 10 min is determined by the method of Paz (refer to Arch.Biochem.Biophys., Vol. 109, page 548(1965)), and the enzymic activity on decomposing 1 micromol of D-threonine at 30° C. is taken as a standard, i.e., one unit (U).

(5) Range of the optimum temperature for the activity:

From the determination of the amount of acetaldehyde produced by the novel enzyme under the conditions of the optimum pH (8.0) at one of a series of temperatures for 10 min. while using a 0.1M tris-HCl buffer solution, it is found that the range of the optimum temperature for the enzyme was 40° to 50° C.

(6) Heat-stability of the novel enzyme:

From the determination of the remaining activity after heating a solution of the novel enzyme in a 0.1M tris-HCl buffer solution at pH of 8.0 for one hour at one of a series of temperatures, it is found that the temperature at which the enzyme is stable was below 40° C.

(7) Conditions of in-activation of the novel enzyme:

The novel enzyme according to the present invention is in-activated completely at a pH below 5 and over 11, and also completely in-activated after heating for one hour at a temperature over 70° C.

(8) Agents inhibiting, activating or stabilizing the activity:

The novel enzyme is activated and stabilized by mercaptoethanol, sodium sulfite, sodium hydrogen sulfite, dithiothreitol, and $Mn^{2+}$, $Co^{2+}$, $Fe^{2+}$ or $Mg^{2+}$, and on the other hand, the activity thereof is inhibited by monovalent $Ag^+$, $Cu^{2+}$, $Hg^{2+}$, $Zn^{2+}$, $Pd^{2+}$, hydroxylamine and p-chloromercuribenzoate.

(9) Coenzyme:

The coenzyme of the enzyme is pyridoxal-5'-phosphate.

(10) Molecular weight:

The molecular weight of the enzyme is in a range of 100,000-150,000 as a result of gel-filtration by Cephadex ® G-200.

(11) Elementary analytical composition:
 50.7–52.7% of carbon,
 6.8–8.8% of hydrogen and
 14.7–16.7% of nitrogen Since the known threonine-aldolase and allothreonine-aldolase decompose only L-threonine and L-allothreonine respectively, and those decomposing the D-isomer have never been known, each enzyme found in the strains respectively is a novel enzyme having a new activity.

Namely, any anzyme have D-threonine-aldolase activity and can be used in the process of the present invention as far as the enzyme can decompose both D-threonine and D-allothreonine to convert them into glycine and acetaldehyde.

L-allothreonine-aldolase used in the process according to the present invention is an enzyme catalyzing L-allothreonine to convert thereof into glycine and acetaldehyde, and the presence thereof has been known in the sheep liver and corn seed in germination, however, the microbiological production thereof has never been known.

However, the present inventors have found out that some bacteria respectively belonging to the genera Bacillus, Pseudomonas, Arthrobacter and Alcaligenes produce the enzyme, and have found the method for producing the enzyme industrially in a large scale. As the examples of the microorganism having the productivity of L-allothreonine-aldolase, a strain of Bacillus DK-315 (deposited in Fermentation Research Institute, Agency of Industrial Science and Technology, Ministry of International Trade and Industry, Japan under a deposite number FERM-P No. 6202) isolated from a soil, a strain of Arthrobacter DK-19 (FERM-P No. 6201), the strain of Pseudomonas DK-2 (FERM-P No. 6200) and a strain of *Alcaligenes faecalis* (deposited in Institute for Fermentation Osaka, Japan under a deposite number of IFO-12669) can be used.

The bacteriological properties of the strain of Bacillus DK-315 (FERM-P No. 6202) are as follows.

(a) Morphological properties:
 (1) Shape and size of the cells: rod-shaped of 0.8 = 2.0 micrometers,
 (2) Pleiomorphism: none,
 (3) Mobility: positive, multitrichous,
 (4) Spore: ellipsoidal in shape existing in the position out from the center,
 (5) Gram-staining: positive,
 (6) Acid-fastness: none.

(b) Growth state in various culture media:
 (1) Plate culture medium of agar with bouillon: favorable with circular colonies,
 (2) Slunt culture of agar with bouillon: favorable, semitransparent with luster,
 (3) Liquid culture medium with bouillon: favorable,
 (4) Stab culture with gelatin and bouillon: favorable filiform in the surface of the culture medium,
 (5) Litmus-milk: decolorated and liquefied.

| (c) Physiological properties: | | |
|---|---|---|
| (1) Reduction of nitrate: | + | |
| (2) Denitrification: | + | |
| (3) MR test: | +(weak) | |
| (4) VP test: | − | |
| (5) Production of indol: | − | |
| (6) Production of H$_2$S: | − | |
| (7) Hydrolysis of starch: | + | |
| (8) Utilization of citric acid | | |
| in Koser's medium: | − | |
| in Christensen's medium: | − | |
| (9) Utilization of inorganic nitrogen | | |
| nitrate: | − | |
| ammonium salt: | + | |
| (10) Production of dye: | − | |
| (11) Activity as urease: | − | |
| (12) Activity as oxidase: | + | |
| (13) Activity as catalase: | +(weak) | |
| (14) Range of growth | | |
| pH: | 5 to 12 | |
| temperature: | 5 to 40° C. | |
| (15) Aerobism: | yes | |
| (16) O-F test (Hush Leifson's method): | F | |
| (17) Production of acid and gas from sugars: | (acid) | (gas) |
| L-arabinose | − | − |
| D-xylose | − | − |
| D-glucose | + | + |
| D-mannose | + | + |
| D-fructose | + | + |
| D-galactose | + | + |
| Maltose | + | − |
| Sucrose | − | − |
| Lactose | − | − |
| Trehalose | + | − |
| D-sorbitol | − | − |
| D-mannitol | + | − |
| Inositol | − | − |
| Glycerol | + | + |
| Starch | + | − |
| (18) Halotrelance in an aqueous 5% sodium chloride solution: | does not grow | |
| (19) Decompositive activity to gelatine: | + | |
| (20) Activity as DNA-ase: | + | |
| (21) Essential vitamins: | none | |

From the above-mentioned bacteriological properties, while referring to "Manual of Determinative Bacteriology, 8th Ed(1974) by Burgey, the strain DK-315 was identified to belong to the genus Bacillus because of moving by peritricha and of gram-positive rod having a capacity of forming spores.

L-allothreonine-aldolase can be produced by culturing each of the above-mentioned strains in a nutrient culture medium which is usually used for culturing a bacterial strain containing a saccharide such as glucose, glycerol and molasses or an organic acid such as acetic acid, malic acid and the like as a carbon source, ammonium sulfate, ammonium chloride, urea and the like as a nitrogen source, and an inorganic ion such as ammonium sulfate, ammonium chloride and urea, as an organic nutrient source of yeast-extract, peptone, meat-extract, corn-steep liquor and the like and a metal salt such as magnesium, iron, manganese, potassium and phosphates usually according to the conventional method of cultivating bacteria at a pH of 4 to 10 for one to three days at 20° to 60° C. aerobically at the pH of the culture medium of 4.0 to 10.0.

Thus, L-allothreonine-aldolase is produced and accumulates in the bacterial bodies, and accordingly, in the case of isolating the enzyme from the cultured medium, the bacterial cells are broken by a known method such as a mechanical means, an enzymic means or a autolysing method and then the crude extract of the enzyme is prepared. The crude extract was treated by a suitable combination of precipitation with ammonium sulfate or a solvent such as acetone or ethanol and chromatography while using ion-exchangers such as DEAE-cepharose, DEAE-cephadex, gel of calcium phosphate or adsorbents to be the enzyme product of a high quality. The followings are the simple physico-chemical properties of the thus purely obtained L-allothreonine-aldolase.

(1) Optimum pH; 8 to 9,
(2) Optimum temperature: 60° to 70° C.,
(3) Conditions for inactivation: inactivated within one hour at 30° C. and pH of 5 to 11 or in one hour at a temperature of higher than 50° C. and pH of 8,
(4) Inhibitants: $Cu^{2+}$, $Hg^{2+}$ and $Ag^{1+}$,
(5) Stabilizers: mercaptoethanol, dithiothreitol and sodium sulfite,
(6) Coenzyme: pyridoxal-5'-phosphate.
Since L-allothreonine-aldolase requires pyridoxal-5'-phosphate as a coenzyme for exhibiting its activity, usually $10^{-3}$ to $10^{-5}$M of pyridoxal-5'-phosphate is made to coexist with the enzyme whenever it is reacted.
(7) Molecular weight: 100,000 to 150,000 according to the determination of gel-filtration by Cephadex ®G-200.
(8) Elementary analytical data:
C: 51.4–53.4%
H: 6.5–8.5% and
N: 14.2–16.2%.

L-allothreonine-aldolase used in the present invention is enough for the purpose if it decomposes L-allothreonine into glycine and acetaldehyde, and it goes without saying that the enzyme is not restricted to that derived from microorganism.

The enzymes used in the present invention, that is, D-threonine-aldolase and L-allothreonine-aldolase, are respectively enough for the purpose in the case where they are respectively under the condition of capable of exhibiting the enzymatic activity thereof, and they are never restricted under isolated condition, and accordingly, half-purified products, crude extract, moreover, the cultured medium, living cells, freeze-dried cells, dried cells by acetone, ground cells, ground sheep liver and the like may be used as it is. The immobilized enzyme or the immobilized cells by a known means can be used. As a method of immobilization, a method of combining with a carrier, a method of cross-linking, a method of entrapping, a method of agglutination and the like are broadly usable.

DL-threonine or a mixture of DL-threonine and DL-allothreonine may be the product obtained by any known method, and for instance, a method wherein an acetoacetate is used as the starting material for obtaining an ester of alpha-amino-beta-hydroxybutyric acid and the amino-hydroxybutyrate is reacted with thionyl chloride to form an oxazoline-ester, and then the ester is hydrolyzed into the product by heating (refer to J.Am.-Chem.Soc., 71, 1101(1949)) and a method wherein vinyl acetate as the starting material is subjected to hydroformylation by the oxo process to give alpha-acetoxypropionaldehyde and the aldehyde is reacted with hydrogen cyanide and ammonia to be alpha-amino-beta-hydroxybutyronitrile which is in turn reacted with phosgen to be a derivative of oxazolidone and then the derivative is subjected to hydrolysis to be the product (refer to Japanese Patent Publication No. 40-11608(1965)) are utilizable for the purpose. However, since in the process according to the present invention, the object product is L-threonine and by-product consists of glycine and acetoaldehyde, a synthetic method which produces the allo-forms in a smaller amount and requires glycine and acetaldehyde as the starting compounds is preferable. In this connection, a method wherein a metal salt is reacted with glycine to be a metal complex of glycine and then acetaldehyde is condensed with the metal complex of glycine (refer to Japanese Patent Publications Nos. 36-19562(1961) and 47-39093(1972)) is the suitable method for producing a mixture of DL-threonine and DL-allothreonine. The solution containing the mixture may be an aqueous solution which is obtained by dissolving the once-obtained product as crystals into water, however, it may be the liquid obtained by the synthesis, or may be any intermediate liquid in the course of obtaining the crystals of the mixture. In short, the liquid containing DL-threonine and DL-allothreonine used in the process according to the present invention may be a solution containing DL-threonine and DL-allothreonine, and the ratio of D-isomer to L-isomer in the solution and the ratio of threonines to allothreonines in the solution are out of the question. Further, the solution may contain any other impurities in addition to DL-threonine and DL-allothreonine. Any impurities inhibiting the enzyme reaction, if any, should be removed in advance. For instance, in the case where a metal ion used in the synthesis is deleterious in the enzyme reaction, it should be removed by a cation-exchanging resin, etc. in advance of the enzyme reaction.

There is no particular difficulty in treating (catalyzing) a solution containing DL-threonine with D-threonine-aldolase or treating (catalyzing) a solution containing both DL-threonine and DL-allothreonine with the mixture of D-threonine-aldolase and L-allothreonine-aldolase. In short, the indicated enzyme may be made present in the aqueous solution of the indicated substance. The concentration of DL-threonine and/or DL-allothreonine in the solution may be an extent which does not remarkably inhibit the enzymatic activity, and it is preferably 0.1 and 2 mol/liter. The solvent of the enzyme reaction system is, in principle, water, however, an organic solvent may be contained if it does not inhibit the enzyme reaction. Although the pH of the reaction system depends on the enzyme, it is preferably around pH 7 to 10 in the cases where the enzyme is obtained in Examples described. Although the reaction temperature depends on the enzyme, it is preferably 30° to 45° C. in the case of using the enzyme prepared in Examples described. In addition, in the case of using the enzyme prepared in Example, the enzyme reaction can be accelerated by bringing $10^{-3}$ to $10^{-5}$ molar amount of pyridoxal-5'-phosphate coexist in the system as a coenzyme. Furthermore, a surfactant may be added to the reaction system for various purposes. The enzyme reaction can be carried out by a batch system or in a continuous system. D-threonine-aldolase and L-allothreonine-aldolase may be added together with or separately.

The reaction time can be selected optionally according to the purpose of L-threonine for use. For example, in the case where L-threonine in which the existence of undecomposed isomer is allowable is to be obtained, the reaction may be stopped before the completion of enzymatic decomposition of the isomer. At any rate, a reaction time of 5 to 100 hours is sufficient for every enzyme.

After the enzyme reaction finishes, the suspending matters in the reaction mixture are removed by centrifugation or filtration, if necessary, and the obtained reaction mixture is purified by treatment of ion-exchanging resin and crystallization, and after decolorizing the reaction solution by activated carbon, etc., the decolorized solution is condensed to obtain the crystals of L-threonine in a pure state. The reaction product other than L-threonine comprises glycine and acetaldehyde in the case of using D-threonine-aldolase and also in the case of using D-threonine-aldolase and L-allothreonine-aldolase, and glycine can be separated and isolated by chromatography, for example, using ion-exchanging resin. Because of the non-enzymatic condensation of acetaldehyde with glycine during the enzyme reaction or of the re-combination with glycine by each enzyme, it may be better to recover acetaldehyde during the enzyme reaction by distillation, etc.

According to the process of the present invention, the removal of D-threonine or DL-allothreonine from threonine mixture which has been difficult can be carried out by one convenient and simple step. Accordingly, the present invention has dissolved the large problem which has hindered the separation of the isomer and has provided with the method for producing L-threonine at a low price from threonine which is synthetically produced. Particularly, when combined with the synthetic method for producing threonine from glycine and acetaldehyde, it is more preferable, because the by-products of the enzyme reaction can be re-used as the starting materials.

The present invention will be more precisely explained while referring to Examples as follows.

However, the present invention is not restricted to Examples under mentioned. From the foregoing description, one skilled in the art can easily ascertain the essential characteristics of this invention, and without departing from the spirit and scope thereof, can make various changes and modifications of the invention to adapt it to various usage and conditions.

In addition, all the percentage are % by weight. The activity of D-allothreonine-aldolase and that of L-allothreonine-aldolase were measured as in the case of measuring the activity of D-threonine-aldolase except for changing the substrate corresponding to each enzyme. The titer of the activity was designated that the activity to decompose 1 micromol of allothreonine, the substrate, for one min is one unit (1 U).

PREPARATION EXAMPLE 1

Production of an enzyme having the activity of D-threoninealdolase and the activity of D-allothreonine-aldolase A culture medium adjusted to pH 7.5 comprising 0.5% of polypeptone, 0.2% of yeast extract, 0.1% of potassium dihydrogen sulfate, 0.05% of magnesium sulfate, 0.1% of L-glutamic acid and 0.5% of D-threonine was prepared, and in a 5-liter culturing vessel, 3 liters of the culture medium was introduced, and then the medium was sterilized at 120° C. for 10 min. In the thus sterilized culture medium, a strain of Arthrobacter DK-19 (FERM-P No. 6201) was inoculated and cultured for 20 hours at 30° C. while aerating and agitating.

After the culturing finished, the cells were collected from the culture liquid by centrifugation, and after washing the cells with aqueous 0.9% sodium chloride solution, the wet cells were suspended in 100 ml of 0.1M phosphate buffer solution containing 10 mM of mercaptoethanol and 0.1 mM pyridoxal-5'-phosphate. After treating the thus obtained cell suspension with an ultrasonics of 20 kHz for each 5 min. in total 5 times, the suspension was centrifuged to collect the supernatant liquid. After adding protamin sulfate to the supernatant liquid to remove nucleic acid, the liquid was fractioned by ammonium sulfate to collect a fraction containing an enzyme having the activity of D-threonine-aldolase.

After subjecting the fraction having activity of D-threonine-aldolase into dialysis against a 0.01M phosphate buffer containing 10 mM of mercaptoethanol and 0.1 mM pyridoxal-5'-phosphate at pH 7.5, the dialyzate was passed through a column filled with 100 ml of DEAE-Cephadex ®A-50 and then the adsorbed fraction on the column was subjected to elution fractionally by a method of concentration-gradient of potassium chloride to collect the fraction containing the enzyme having the activity of D-threonine-aldolase. By condensing the fraction while using a method of ultrafiltration, 10 ml of a solution of the purified D-threonine-aldolase was obtained. The activity of D-threonine-aldolase and the activity of D-allothreonine-aldolase of the thus obtained solution were 5 U/ml and 12.5 U/ml, respectively.

PREPARATION EXAMPLE 2

Production of enzymes having the activity of D-threoninealdolase and the activity of D-allothreonine-aldolase A strain of Pseudomonas DK-2 (FERM-P No. 6200) and a strain of *Alcaligenes faecalis* IFO 12669 were respectively cultured in the same kind of culture medium by the same procedures as in Preparation Example 1, and from the thus cultured medium, each 10 ml of a solution of purified D-threonine-aldolase was obtained by the same procedures in Preparation Example 1. The activity of D-threonine-aldolase and the activity of D-allothreonine-aldolase of the enzyme obtained by culturing the strain of Pseudomonas DK-2 were 4.5 U/ml and 10.8 U/ml, respectively, and those obtained by culturing the strain of *Alcaligenes faecalis* were 4.2 U/ml and 9.5 U/ml, respectively.

PREPARATION EXAMPLE 3

Production of L-allothreonine-aldolase

A strain of Bacillus DK-315 (FERM-P No. 6202) was cultured in the same culture medium and in the same manner as in Preparation Example 1, and 10 ml of aqueous solution of purified L-allothreonine-aldolase was obtained by the same procedures of isolation and purification as Preparation Example 1. The activity of L-allothreonine-aldolase of the thus obtained solution was 4.5 U/ml, and the solution showed no activity at all on D-allothreonine and D-threonine.

SYNTHESIS EXAMPLE 1

Synthesis of DL-threonine

Into 5 liters of hot water, 75 g of glycine was dissolved, and 100 g of basic copper carbonate was slowly added to the solution and the mixture was reacted by heating. After the reaction finished, an excess of basic copper carbonate was filtered off from the hot solution, and after condensing the filtrate under a reduced pressure, the concentrated filtrate was cooled to obtain 110 g of crystalline copper-glycine complex.

Into one liter of water, 58 g of copper salt of glycine, 40 of an anion-exchange resin SA 21A ($HCO_3$-type) and 45 ml of acetaldehyde were added, and the mixture was brought into reaction by heating to 40° C. for 2 hours under agitation. After the reaction was over, the reaction mixture was left as it is at 5° C. for 24 hours to obtain crystals of bisacetaldehydethreonine copper-complex separated out. After collecting the crystals together with the catalyst by filtration, the solid matters were suspended in 0.6 liter of an aqueous 3% ammonia solution and the suspension was filtered. The filtrate was passed through a column filled with 1.2 liters of a chelate resin, Dowex ®A-1 ($NH_4$-type), to remove copper from the filtrate, and the fraction reacting positively to ninhydrin was collected and condensed under a reduced pressure. By adding methanol to the condensate, crystals were obtained and recrystallized from aqueous methanolic solution to be 41 g of DL-threonine not containing allothreonine at all.

SYNTHESIS EXAMPLE 2

Synthesis of a mixture of DL-threonine and DL-allothreonine

Into 5 liters of hot water, 75 g of glycine was dissolved, and 100 g of basic copper carbonate was slowly added to the solution and the mixture was reacted by heating. After the reaction finished, an excess of basic copper carbonate was filtered off from the hot solution, and after condensing the filtrate under a reduced pressure, the concentrated filtrate was cooled to obtain 110 g of crystalline copper-glycine complex.

Into 0.8 liter of methanol containing 6 g of potassium hydroxide, 58 g of copper-glycine complex and 50 g of acetaldehyde were added to react at 50° to 60° C. for 1.5 hours under agitation. After the reaction was over, the reaction mixture was filtered to remove a small amount of undissolved material, and after adding 6.4 g of acetic acid to the filtrate, it was subjected to distillation under a reduced pressure to remove the solvent. After sufficiently washing the crude copperthreonine compound which remained as a distillation residue with water, the crystalline compound was disolved in 0.5 liter of 6N aqueous ammonia solution, and the solution was passed through a column filled with 2 liters of Dowex ® A-1 ($NH_4$-type), a chelating resin, to remove copper from the solution and collect the fraction containing threonine. The fraction was condensed under a reduced pressure to 100 ml, and 400 ml of methanol was added to the condensate, and then the mixture was cooled to obtain crystals which were recrystallized from aqueous methanolic solution to be 38 g of crystalline DL-threonine containing 10% of DL-allothreonine.

EXAMPLE 1

Into 20 ml of an aqueous solution containing $10^{-6}$ mol of pyridoxal-5'-phosphate, $10^{-4}$ mol of mercaptoethanol, $10^{-3}$ mol of manganese chloride and 2.38 g of the crystals of DL-threonine which was obtained in Synthesis Example 2 and contained 10% of DL-allothreonine, 10 ml of the solution containing the purified enzyme which was obtained in Preparation Example 1 and had both the activity of D-threonine-aldolase and the activity of D-allothreonine-aldolase and 10 ml of the solution of purified D-allothreonine-aldolase which was obtained in Preparation Example 3 were added, and while subjecting the mixture to distillation under a reduced pressure to remove and recover acetaldehyde formed in the enzyme reaction, the mixture was brought into reaction at 30° C. for 24 hours. The pH of the reaction mixture during reaction was kept at 7.5 to 8.5 by adding 0.1N sodium hydroxide solution.

After the reaction finished, the reaction mixture was neutralized with dilute hydrochloric acid, and the neutralizate was passed through a column filled with 100 ml of Dowex® 50 WX-8 of H+-type. The column was washed with water, and threonine, glycine etc. which had been adsorbed onto the column were eluted with aqueous 0.2N ammonia solution. After condensing the eluate to dryness under a reduced pressure, the residual solid matter was dissolved in 20 ml of water, and after adjusting the pH of the solution with dilute hydrochloric acid to 3, the solution was again passed through a column filled with 100 ml of Dowex® 50 WX-8 of H+-type. After washing the column with water, aqueous 0.1N ammonia solution was passed through the column to elute a fraction containing threonine and the eluate was dried to solid under a reduced pressure. The solid matter was dissolved in 4 ml of water and 10 ml of ethanol was slowly added to the solution to obtain crystals which were isolated. The dry weight of the crystals was 0.9 g and it was confirmed by paper-chromatography that the crystals were pure threonine. The specific rotation of the crystal was $[\alpha]_D^{27} = -28.7°$(in water) which was coincided with that of the authentic specimen of pure L-threonine.

The aqueous 0.1N ammonia was further passed through the remaining column to elute a fraction containing glycine. The eluate was dried to solid under a reduced pressure, and the solid matter was dissolved in 1 ml of water. By adding 4 ml of ethanol slowly to the solution, crystals appeared in the solution, which were isolated and dried to be 0.65 g of glycine after confirming by paper-chromatography.

On the other hand, acetaldehyde recovered during the reaction under a reduced pressure was 0.34 g.

Example 2

In the same manner as in Example 1 except for using 10 ml of the solution of purified D-threonine-aldolase obtained from Pseudomonas DK-2 FERM-P 6200 in Preparation Example 2 instead of the solution of purified D-threonine-aldolase obtained in Preparation Example 1, decomposition of DL-threonine containing 10% of DL-allothreonine was carried out to obtain 0.91 g of crystals of threonine not containing allothreonine at all, 0.66 g of crystalline glycine and 0.34 g of acetaldehyde. The specific rotation of the crystalline threonine was $[\alpha]_D^{27} = -28.7°$(in water), namely showing that the crystals consisting only of L-threonine.

Example 3

In the same manner as in Example 1 except for using 10 ml of the solution of purified D-threonine-aldolase obtained from *Alcaligenes faecalis* IFO 12669 in Preparation Example 2 instead of the solution of D-threonine-aldolase obtained in Preparation Example 1, decomposition of DL-threonine containing 10% of DL-allothreonine was carried out followed by the operation of isolation. Thus, 0.91 g of crystalline threonine not containing allothreonine at all, 0.66 g of crystalline glycine and 0.34 g of acetaldehyde were obtained. The specific rotation of the crystalline threonine was $[\alpha]_D^{27} = -28.7°$(in water), showing that the crystals consisting only of L-threonine.

Example 4

Into 30 ml of an aqueous solution containing 2.38 g of DL-threonine obtained in Synthesis Example 1, $10^{-6}$ mol of pyridoxal-5'-phosphate, $10^{-4}$ mol of mercaptoethanol, $10^{-3}$ mol of manganese chloride, 10 ml of the solution of purified D-threonine-aldolase obtained in Preparation Example 1 was added and while removing and recovering acetaldehyde formed during the enzymatic reaction, the mixture was brought into reaction at 30° C. for 24 hours. The pH of the reaction system was kept at 7.5 to 8.5 by adding aqueous 0.1N sodium hydroxide solution.

After the reaction finished, the reaction mixture was neutralized with dilute hydrochloric acid and passed through a column filled with 100 ml of Dowex®50 WX-8 (H+-type). After washing the column with water, threonine and glycine adsorbed onto the column were eluted with aqueous 0.2N ammonia solution. After drying the eluate to solid under a reduced pressure, the solid matter was dissolved in 20 ml of water, and the solution was adjusted to pH 3 by addition of dilute hydrochloric acid and then passed through the column filled with 100 ml of Dowex®50 WX-8 (H+-type). After washing the column with water, aqueous 0.1N ammonia solution was passed through the washed column to elute the fraction containing threonine. The eluate was dried to solid under a reduced pressure, and then the solid matter was dissolved in 4 ml of water. By adding 10 ml of ethanol slowly to the solution, crystals appeared in the solution, which were isolated and dried. The thus obtained crystals weighing 0.95 g were confirmed to be pure threonine having a specific rotation of $[\alpha]_D^{27} = -28.7°$ (in water) coinciding with that of the authentic specimen of L-threonine.

The solution of 0.1N ammonia was further passed through the above-mentioned column to elute the fraction containing glycine, and the eluate was condensed to dryness under a reduced pressure. After dissolving the solid matter in 1 ml of water, 4 ml of ethanol was slowly added to the solution to obtain crystals separating out. After drying, the crystals were weighed to be 0.6 g which consisted solely of glycine according to the paper-chromatography. On the other hand, the recovered acetaldehyde during the reaction under a reduced pressure was 0.3 g.

Example 5

The same procedures of the enzymatic reaction and separation of the products were carried out as in Example 1 except for not carrying out the distillation under a reduced pressure during the enzymatic reaction. As a result, 0.8 g of crystalline threonine containing 10% of allothreonine, 0.3 g of crystalline glycine and 0.05 g of acetaldehyde were obtained.

Example 6

The strain of Pseudomonas DK-2 (FERM-P No. 6200) was cultured in the same conditions as in Preparation Example 1 and the thus obtained fraction amounting to 10 ml having the activity of D-threonine-aldolase and the thus obtained fraction amounting to 10 ml having the activity of L-allothreonine-aldolase were respectively condensed by ultrafiltration to obtain two kinds of solutions, respectively containing D-threonine-aldolase and L-allothreonine-aldolase.

By adding the thus obtained two kinds of solutions into a mixture of 2 g of DL-threonine and 1 g of DL-allothreonine in the same conditions as in Example 1 except for a temperature of 35° C. instead of 30° C. in Example 1, 0.85 g of crystalline L-threonine not containing D-threonine nor DL-allothreonine, 1.01 g of glycine and 0.51 g of acetaldehyde were obtained. The specific rotation of the thus obtained L-threonine was $[\alpha]_D^{27} = -28.6°$ (in water).

What is claimed is:

1. A process for preparing L-threonine which comprises causing D-threonine-aldolase, or D-threonine-aldolase and L-allothreonine-aldolase to act on a solution containing at least DL-threonine.

2. A process according to claim 1, wherein said solution is a solution of DL-threonine.

3. A process according to claim 1, wherein said solution is a solution of a mixture of DL-threonine and DL-allothreonine.

4. A process according to claim 2, wherein said solution is treated with D-threonine-aldolase.

5. A process according to claim 4, wherein said solution is treated with D-threonine-aldolase and L-allothreonine-aldolase.

6. A process according to claim 4, wherein said D-threonine-aldolase is an enzyme having an activity of decomposing D-threonine and D-allothreonine asymmetrically into glycine and acetaldehyde.

7. A process according to claim 5, wherein said L-allothreonine-aldolase is an enzyme having an activity of decomposing L-allothreonine asymmetrically into glycine and acetaldehyde.

8. A process according to claim 6, wherein said enzyme is a product of a strain of microorganism belonging to the genus Arthrobacter, Pseudomonas or Alcaligenes.

9. A process according to claim 7, wherein said L-allothreonine-aldolase is a product of a strain of microorganism belonging to the genus Bacillus, Arthrobacter, Pseudomonas or Alcaligenes.

* * * * *